(12) United States Patent
Pompetzki et al.

(10) Patent No.: US 6,930,213 B1
(45) Date of Patent: Aug. 16, 2005

(54) PROCESS FOR THE HYDROGENATION OF ACETONE

(75) Inventors: Werner Pompetzki, Dorsten (DE); Joachim Schuler, Marl (DE); Dietrich Maschmeyer, Recklinghausen (DE)

(73) Assignee: Phenolchemie GmbH & Co. KG, Gladbeck (DE)

( * ) Notice: Subject to any disclaimer, the term of this patent is extended or adjusted under 35 U.S.C. 154(b) by 761 days.

(21) Appl. No.: 09/618,044

(22) Filed: Jul. 17, 2000

(30) Foreign Application Priority Data

Jul. 17, 1999 (DE) ................................ 199 33 691

(51) Int. Cl.[7] .................... C07C 29/145; C07C 29/143; C07C 29/136
(52) U.S. Cl. ...................... 568/883; 568/881; 568/882
(58) Field of Search ............................... 568/881, 882, 568/883

(56) References Cited

U.S. PATENT DOCUMENTS

| | | | |
|---|---|---|---|
| 2,983,734 A | * 6/1961 | Sargent | 260/347.8 |
| 3,978,149 A | * 8/1976 | Mertzweiller et al. | 260/683.9 |
| 4,626,604 A | * 12/1986 | Hiles et al. | 568/881 |
| 5,081,321 A | * 1/1992 | Fukuhara et al. | 568/881 |
| 5,684,215 A | * 11/1997 | Horn et al. | 568/881 |

FOREIGN PATENT DOCUMENTS

| | | |
|---|---|---|
| EP | 0 379 323 | 7/1990 |
| EP | 0 652 200 | 5/1995 |
| EP | 0 661 257 | 7/1995 |
| EP | 0 665 207 | 8/1995 |
| EP | 0 694 518 | 1/1996 |

OTHER PUBLICATIONS

Sigma Chem. Co., Biochem., Org. Compds. for research and Diagnostic Reagents, 1994, pp. 1681.*

* cited by examiner

*Primary Examiner*—Elvis O. Price
(74) *Attorney, Agent, or Firm*—Oblon, Spivak, McClelland, Maier & Neustadt, P.C.

(57) ABSTRACT

Acetone is hydrogenated by a process comprising, conducting the liquid-phase hydrogenation of acetone in at least two hydrogenation process stages, thereby preparing isopropanol product with a high selectivity and in high purity.

15 Claims, 2 Drawing Sheets

US 6,930,213 B1

PROCESS FOR THE HYDROGENATION OF ACETONE

BACKGROUND OF THE INVENTION

1. Field of the Invention

The present invention relates to a process for the hydrogenation of acetone to give isopropanol.

2. Description of the Background

Acetone is a large-volume industrial product and can be prepared in specific ways, e.g. by oxidation of propane, or as a coproduct in the Hook phenol synthesis.

In the Hook phenol synthesis, one molecule of acetone is obtained per molecule of phenol. The demand for phenol is very different from that for acetone. For example, phenol and acetone are consumed in a ratio of 2:1 in the synthesis of bisphenol A.

A possible downstream product of acetone is isopropanol which has a significantly broader range of use. A very significant proportion of the isopropanol is converted into ethers, in particular diisopropyl ether and tert-butyl isopropyl ether.

The conversion of acetone into isopropanol is generally conducted by catalytic hydrogenation. For the production of isopropanol ethers, processes of hydrogenation and etherification are combined. Thus, EP 0 694 518, EP 0 665 207, EP 0 652 200 and EP 0 661 257 disclose processes for preparing various isopropyl ethers. The disclosures of these patent applications involve the following process sequence:

a) Catalytic hydrogenation of an acetone-containing liquid phase.
b) Etherification of the resulting isopropanol over acid catalyst systems.

The process steps a) and b) are conducted one after the other, i.e. without work-up of the product mixture obtained from a).

Furthermore, EP 0 665 207 teaches a single-stage process in which a) and b) are conducted by means of a suitable combination catalyst in a single reactor. Because of by-product formation (the processes are designed for the preparation of isopropyl ether), isolation of the isopropanol after the reaction step a) is very costly.

The process described in EP 0 379 323 is a better method of preparing isopropanol from acetone. In this process, acetone is catalytically hydrogenated at a temperature of from 20 to 200° C. at pressures of from 1 to 80 bar using, as a matter of necessity, a trickle reactor. Trickle reactors are used in order to create a high mass transfer area between liquid and gas. They therefore have to have a trickle surface having a large surface area. The quality of the isopropanol obtained and the amount of by-products is not discussed.

For many applications, isopropanol must not contain by-products such as isopropyl ether nor traces of solvent from the hydrogenation of acetone. This is particularly true in the case where isopropanol is used in medical and cosmetic applications for the preparation of downstream products where isopropanol of a very high degree of purity is required. High degrees of purity can be achieved on an industrial scale only upon the implementation of costly purification steps. Thus, for example, when isopropanol is prepared by introduction of water into propane, sulfur-containing compounds which are present in the isopropanol product can prevent its use in the cosmetic or pharmaceutical industry. Removal of these contaminating components is only possible by further treatment of the isopropanol with activated carbon, $Al_2O_3$ or metals such as copper or nickel. A need continues to exist for a method of producing higher purity isopropanol by the hydrogenation of acetone.

SUMMARY OF THE INVENTION

Accordingly, one object of the present invention is to provide a process for more efficiently hydrogenating acetone to yield highly pure isopropanol.

Briefly, this object and other objects of the present invention as hereinafter will become more readily apparent can be attained by a process for preparing isopropanol of high purity, which comprises:

hydrogenating acetone in the liquid-phase in at least two hydrogenation process stages, thereby preparing isopropanol product.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
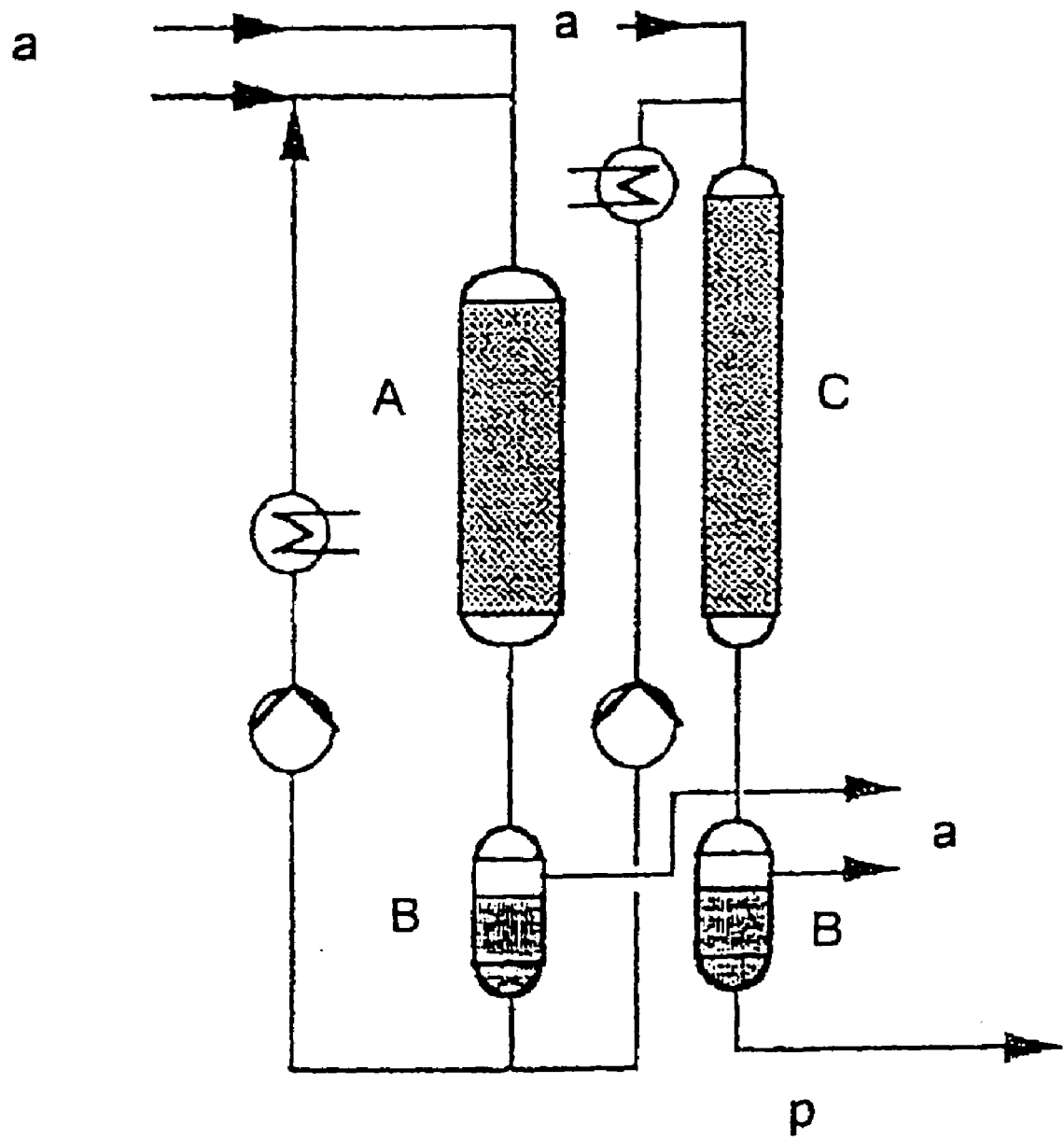
FIG. 1 is a schematic diagram of the invention showing the hydrogenation of acetone in two reactors which are a circulation reactor and a shaft oven.

It has now been surprisingly found that acetone can be hydrogenated in a multistage process to give isopropanol product of high purity.

The process of the invention can be used for the industrial-scale preparation (>100,000 metric tons per annum) of isopropanol from acetone. The formation of by-products is virtually completely avoided so that complicated post-reaction processing is unnecessary.

The present invention accordingly provides a process for the hydrogenation of acetone to isopropanol product, wherein hydrogenation is conducted by liquid-phase hydrogenation in at least two stages.

The following reactions can occur in the hydrogenation of acetone:

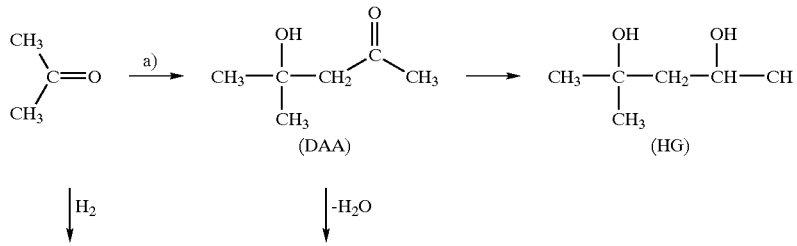

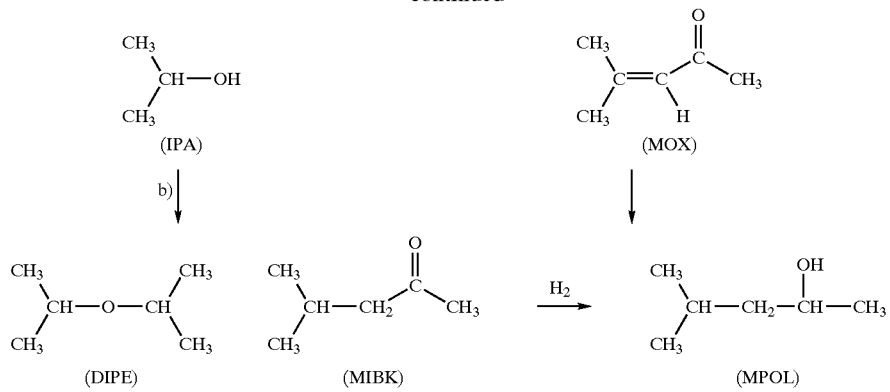

After the alkali-catalyzed aldol condensation a) of acetone to diacetone alcohol (DAA), elimination of water leads to 4-methyl-3-penten-2-one (mesityl oxide, MOX). The hydrogenation of the intermediate MOX leads via 4-methyl-2-pentanone (methyl isobutyl ketone, MIBK) to 4-methyl-2-pentanol (MPOL). However, DAA can also be hydrogenated directly to hexylene glycol (HG). The desired product IPA can also react further with elimination of water b) to form the undesired diisopropyl ether (DIPE).

A suitable catalyst for the reaction should, if possible, be one which functions under neutral reaction conditions so that it does not catalyze the undesirable secondary reaction of IPA, the aldol condensation and the subsequent elimination of water.

Some of the abovementioned secondary reactions proceed with elimination of water. In order to suppress these secondary reactions, i.e. in order to increase selectivity, the addition of a small amount of water is therefore conceivable. This addition of water, which is undesirable in some specific uses of the isopropanol, remains in the product mixture and may have to be removed.

In contrast, the present invention makes it possible to hydrogenate acetone containing a very small amount of water. This is all the more surprising, since in the abovementioned literature, an addition of water to the feed stream is necessary in order to increase selectivity or to reduce by-product formation.

In the process of the invention, acetone having a water content of less than or equal to 1.0% by weight, preferably less than or equal to 0.5% by weight, very particularly preferably 0.2% by weight can be hydrogenated to form isopropanol.

The high conversions sought in industrial-scale processes can in the present case be achieved either by means of circulation reactors or reactors in cascade connected in series.

The multistage process of the invention enables acetone to be hydrogenated to give isopropanol of high purity. The individual, parallel and/or cascade process stages can be configured as circulation reactors or tube reactors.

The reaction conditions can be varied within wide limits. That is; the liquid-phase hydrogenation can be conducted at a temperature of 60 to 140° C., preferably 70 to 130° C., and a pressure of 20 to 50 bar, preferably 25 to 35 bar. The temperature and pressure conditions can differ in the various process stages.

In general, an excess of hydrogen is employed; the molar ratio of hydrogen to acetone ranging from 1.5:1 to 1:1.

In a specific embodiment of the process of the invention, the hydrogenation reaction is conducted in two process stages where the reactor of the 1 st process stage is configured as a circulation reactor and the reactor of the 2nd process stage is configured as a tube reactor.

A simplified flow diagram of an embodiment of the process of the invention together with a few optional components is shown in FIG. 1.

The flow scheme shows upstream circulation reactor A with the ability to recycle product. The conversion which occurs here is a major part of the required hydrogenation conversion. Reactor A operates at a high concentration level and can be operated using a small circulation ratio The product from the circulation reactor can then be subjected to intermediate cooling in apparatus component (B). The hydrogenation in the final conversion step is conducted in a shaft oven (C) which operates as a tube reactor without product recirculation. The hydrogen feed and discharge lines are denoted by a) and the product line is denoted by p). Both reactors A and C are designed as adiabatic reactors.

The starting temperature of the first process stage is advantageously ranges from 50 to 90° C. and the total pressure ranges from 10 to 30 bar. If the catalyst has a high initial activity, it is possible either to reduce the starting temperature or to increase the circulation ratio in the first reactor so as to be able to set the outlet temperature to correspond to the inlet temperature of the second reactor.

The reactor of the first process stage can be operated as a circulation reactor with a circulation ratio ranging from 6 to 10. The concentration of acetone in the circulating stream drops by from 8 to 20% by weight while the concentration of isopropanol increases by the corresponding amount. The hydrogenation reaction is exothermic so that cooling should be provided in or downstream of the circulation reactor. The liquid-phase hydrogenation of the first process stage can be conducted at a temperature ranging from 60 to 130° C., preferably from 80 to 120° C., and a pressure ranging from 20 to 50 bar, preferably from 25 to 35 bar.

The second process stage, which is operated with the characteristics of a tube reactor, can be conducted at a temperature ranging from 60 to 140° C., preferably from 70 to 130° C., and a pressure ranging from 20 to 50 bar.

The same hydrogenation catalyst can be used in the different process stages. Suitable catalysts include commercial hydrogenation catalysts comprising Cu, Cr, Ru or Ni as the active component on a $Al_2O_3$, $TiO_2$ or $ZrO_2$ support. In the process of the invention, nickel-containing catalysts, e.g.

comprising about 10% by weight of nickel on a neutral support, have been found to be useful.

The support material for the catalyst should in all cases be neutral. Neutral support materials include, for example, $\alpha\text{-Al}_2\text{O}_3$, $\text{TiO}_2$, $\text{ZrO}_2$ and mullite.

The process of the invention provides isopropanol of high purity. The total concentration of the by-products formed in the hydrogenation, e.g. 4-methyl-3-penten-2-one, 4-methyl-2-pentanol, diacetone alcohol, hexylene glycol and diisopropyl ether, can be less than 300 ppm, preferably less than 200 ppm, very particularly preferably less than 100 ppm.

The multistage reactor concept offers further advantages because of its high flexibility. Circulation ratio, pressure and temperature can be set independently in the reactors. Should the catalyst activity in a reactor decrease, it is possible, for example, to allow a correspondingly higher temperature in the next reactor.

When designing the reactors, good liquid distribution or a high gas exchange area should be ensured. This can be achieved by means of a suitable liquid distributor, e.g. Raschig rings, wire mesh or Sulzer mixers, and a sufficiently high throughput per unit cross-sectional area (viz. linear velocity) of at least 30 $\text{m}^3/\text{m}^2\cdot\text{h}$.

Having now generally described this invention, a further understanding can be obtained by reference to certain specific examples which are provided herein for purposes of illustration only and are not intended to be limiting unless otherwise specified.

EXAMPLE

Figure 2:
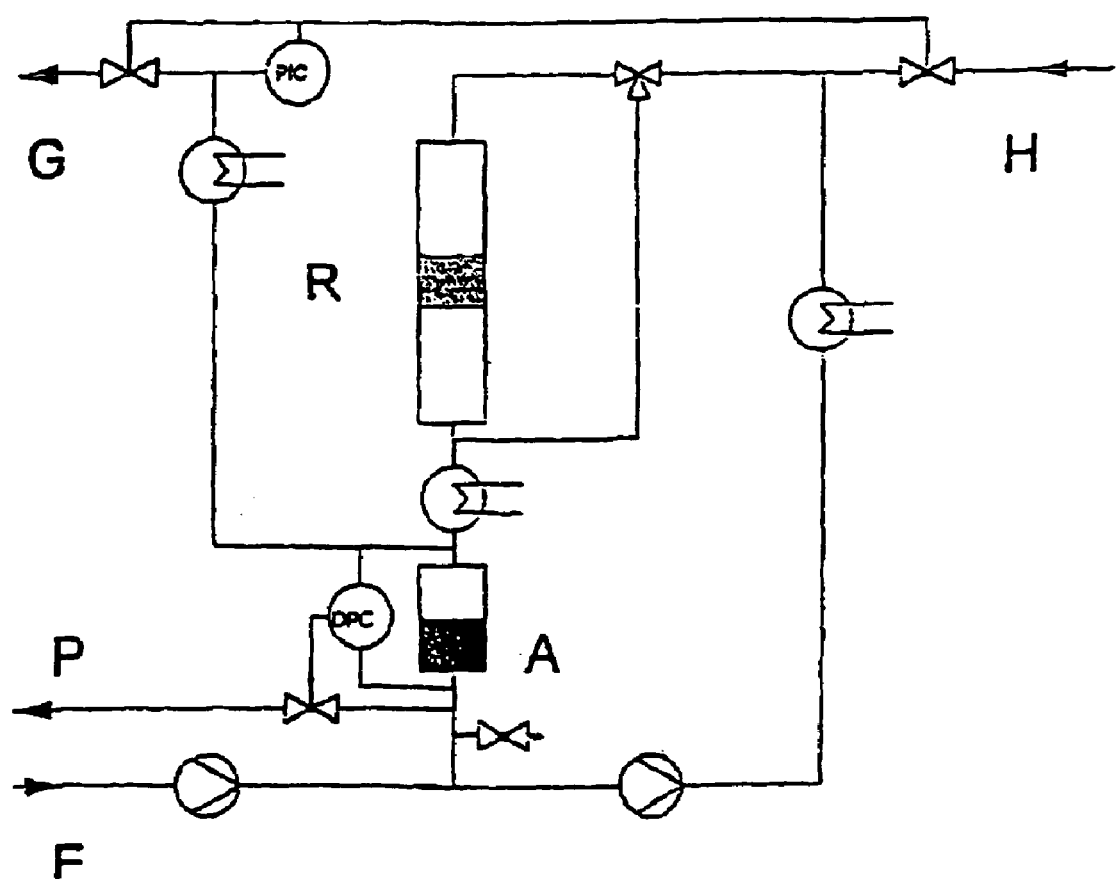
FIG. 2 is a schematic diagram showing the batchwise hydrogenation of acetone.

An experimental plant as shown in FIG. 2 was set-up.

In batchwise experiments, starting material F is allowed to flow into separation vessel A and is pumped around the circuit of the scheme and in the process by-passes reactor R. The apparatus including the reactor is subsequently brought to the desired reaction conditions. At the commencement of the reaction, appropriated switches are turned so as to permit the flow of material in the circuit to flow the reactor R. After about 5 minutes, constant temperature and pressure have become established and the first product samples are taken. Hydrogen is introduced into the reactor and is discharged from the system via lines H and G, respectively. Using different suitable catalyst weights in the reactor, the pump circulation of material yields product at different conversions on a single pass through the catalyst bed of the reactor. Furthermore, isothermal operation is guaranteed, which simplifies the kinetic evaluation of the experiments. Taking samples at various times during the experiment enables a concentration-contact time curve to be recorded. Such experiments correspond to the reactor engineering model of a discontinuously operated stirred tank or a tube reactor.

A nickel-containing catalyst (10% by weight of nickel) on a neutral $\alpha\text{-Al}_2\text{O}_3$ support was used.

Experimental Results:

|  | Percent by weight at inlet | Percent by weight at outlet |
| --- | --- | --- |
| Circulation reactor of the 1st process stage: | | |
| Inlet temperature 70° C. | | |
| Outlet temperature 115° C. | | |
| Circulation ratio 1:8 | | |
| Linear velocity 220 m/h | | |
| Acetone | 22.2 | 12.5 |
| Isopropanol | 77.8 | 87.5 |
| Tube reactor of the 2nd process stage: | | |
| Inlet temperature 70° C. | | |
| Outlet temperature 126° C. | | |
| Linear velocity 38 m/h | | |
| Acetone | 12.5 | 0.54 |
| Isopropanol | 87.5 | 99.45 |
| By-products | | <100 ppm |

By-products of the hydrogenation reaction include: methyl isobutyl ketone, 4-methyl-2-pentanol, hexylene glycol and other high-boilers whose identities were not determined.

The disclosure of German priority application Serial Number 199 33 691.1 filed Jul. 17, 1999 is hereby incorporated by reference into the present application.

Obviously, numerous modifications and variations of the present invention are possible in light of the above teachings. It is therefore to be understood that within the scope of the appended claims, the invention may be practiced otherwise than as specifically described herein

What is claimed as new and is intended to be secured by Letters Patent is:

1. A process for the hydrogenation of acetone, which comprises:
   conducting the liquid-phase hydrogenation of acetone having a water content of less than or equal to 1.0% by weight in at least two hydrogenation process stages, thereby preparing isopropanol product.

2. The process as claimed in claim 1, wherein the liquid-phase hydrogenation in a first stage is conducted at a temperature of 60 to 140° C. and a pressure of 20 to 50 bar.

3. The process as claimed in claim 1, wherein the acetone to be hydrogenated has a water content of less than or equal to 0.5% by weight.

4. The process as claimed in claim 3 wherein the acetone to be hydrogenated has a water content of less than or equal to 0.2% by weight.

5. The process as claimed in claim 1, wherein the liquid-phase hydrogenation reaction is conducted in the presence of a nickel containing catalyst on a neutral support.

6. The process as claimed in claim 5, wherein said neutral support is $\alpha\text{-Al}_2\text{O}_3$.

7. The process as claimed in claim 2, wherein the liquid-phase hydrogenation is conducted at a temperature of 70 to 130° C., and a pressure of 25 to 35 bar.

8. The process as claimed in claim 1, wherein the liquid-phase hydrogenation in a second stage is conducted at a temperature of 60 to 140° C. and a pressure ranging from 20 to 50 bar.

9. The process as claimed in claim 8, wherein the liquid-phase hydrogenation is conducted at a temperature of 70 to 130° C.

10. The process as claimed in claim 1, wherein the hydrogenation is conducted at a molar ratio of hydrogen to acetone ranging from 1.5:1 to 1:1.

11. The process as claimed in claim 1, wherein the total concentration of by-products formed in said liquid-phase hydrogenation reaction is less than 300 ppm.

12. The process as claimed in claim 11, wherein said total amount of by-products is less than 200 ppm.

13. The process of claim 12, wherein the total amount of by-products is less than 100 ppm.

14. The process as claimed in claim 1, wherein the liquid-phase hydrogenation reaction is conducted in the presence of a hydrogenation catalyst of copper, chromium, ruthenium or nickel on a $Al_2O_3$, $TiO_2$ or $ZrO_2$ support.

15. The process as claimed in claim 1, wherein the liquid-phase hydrogenation reaction is conducted in the presence of a hydrogenation catalyst of a catalytically active metal on a neutral support selected from the group consisting of $\alpha$-$Al_2O_3$, $TiO_2$, $ZrO_2$ or mullite.

* * * * *